United States Patent
Xu et al.

(10) Patent No.: US 12,222,332 B2
(45) Date of Patent: Feb. 11, 2025

(54) DEVICE FOR HIGH TEMPERATURE FATIGUE TEST AND METHOD FOR HIGH TEMPERATURE FATIGUE TEST OF RESIN CONCRETE

(71) Applicant: Ningbo Roaby Technology Industrial Group Co., Ltd., Ningbo (CN)

(72) Inventors: Bin Xu, Ningbo (CN); Su Xu, Ningbo (CN); Qi You, Ningbo (CN)

(73) Assignee: NINGBO ROABY TECHNOLOGY INDUSTRIAL GROUP CO., LTD., Ningbo (CN)

( * ) Notice: Subject to any disclaimer, the term of this patent is extended or adjusted under 35 U.S.C. 154(b) by 290 days.

(21) Appl. No.: 17/889,334

(22) Filed: Aug. 16, 2022

(65) Prior Publication Data

US 2023/0084428 A1 Mar. 16, 2023

(30) Foreign Application Priority Data

Aug. 16, 2021 (CN) .......................... 202110938867.1
Feb. 14, 2022 (CN) .......................... 202210132314.1

(51) Int. Cl.
*G01N 3/36* (2006.01)

(52) U.S. Cl.
CPC ....... *G01N 3/36* (2013.01); *G01N 2203/0044* (2013.01); *G01N 2203/0048* (2013.01); *G01N 2203/0073* (2013.01); *G01N 2203/0226* (2013.01)

(58) Field of Classification Search
CPC ............. G01N 3/36; G01N 2203/0044; G01N 2203/0048; G01N 2203/0073; G01N 2203/0226; G01N 17/00; G01N 3/20; G01N 2203/0005; G01N 2203/0282; G01N 2203/0694; G01N 33/383; G01N 3/00; G01M 5/0033; G01M 5/0008
See application file for complete search history.

(56) References Cited

U.S. PATENT DOCUMENTS 5,415,047 A * 5/1995 Maciejewski ............ G01N 3/04
73/856

FOREIGN PATENT DOCUMENTS

| CN | 105181493 | A | * | 12/2015 | |
|---|---|---|---|---|---|
| CN | 108426765 | A | * | 8/2018 | ............... G01N 3/00 |
| CN | 109932258 | A | * | 6/2019 | |
| CN | 209821039 | U | * | 12/2019 | |

(Continued)

*Primary Examiner* — Francis C Gray
(74) *Attorney, Agent, or Firm* — MATTHIAS SCHOLL P.C.; Matthias Scholl

(57) ABSTRACT

A device for fatigue test includes a sample-laying part, a sample support, and a force-applying part. The sample-laying part is disposed on the sample support; and the force-applying part is disposed on the sample-laying part; the sample-laying part includes a substrate plate and at least two arms disposed on the substrate plate; the sample support includes a bed plate and at least four roller assemblies disposed on the bed plate; each roller assembly includes a roller, a roller support, and an adjusting bolt; the roller support is disposed on the bed plate; the roller is disposed on the roller support; the adjusting bolt is disposed between the roller and the roller support; and the sample support further includes at least one barrier, and both ends of the barrier are connected to two adjacent roller supports, respectively.

8 Claims, 3 Drawing Sheets

(56) References Cited

FOREIGN PATENT DOCUMENTS

| | | | | | |
|---|---|---|---|---|---|
| CN | 112697576 | A | * | 4/2021 | ............... G01N 3/02 |
| CN | 113758818 | A | * | 12/2021 | ............... G01N 3/36 |
| CN | 117589608 | B | * | 4/2024 | |

* cited by examiner

DEVICE FOR HIGH TEMPERATURE FATIGUE TEST AND METHOD FOR HIGH TEMPERATURE FATIGUE TEST OF RESIN CONCRETE

CROSS-REFERENCE TO RELATED APPLICATIONS

Pursuant to 35 U.S.C. § 119 and the Paris Convention Treaty, this application claims foreign priority to Chinese Patent Application No. 202110938867.1 filed Aug. 16, 2021, and to Chinese Patent Application No. 202210132314.1 filed Feb. 14, 2022. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, MA 02142.

BACKGROUND

The disclosure relates to the field of bridge load testing, and more particularly to a device and method for high temperature fatigue test of resin concrete.

Pavement structure is an important protective layer for a steel bridge deck. The service life of the pavement structure under a cyclic loading is determined by a variety of factors, including the collaborative deformability of the steel bridge deck and the protective layer, as well as the fatigue cracking resistance of the protective layer. Conventional fatigue test methods are suitable for certain paving materials, but the measurements are inaccurate and unreliable. In addition, the conventional fatigue test is often carried out at temperatures ranging from 15° C. to 25° C. In a higher temperature, such as 60° C. to 90° C., the conventional fatigue test faces many challenges. Particularly, for resin concrete, the structural diversity and the material particularity thereof make the traditional fatigue test methods unable to meet the requirements of the fatigue test of resin concrete.

SUMMARY

The disclosure provides a device and method for fatigue test of resin concrete at 60-90° C. The fatigue test method is performed to accurately measure strength of different types of concrete slabs at a controlled temperature.

A device for fatigue test comprises a sample-laying part, a sample support, a force-applying part; the sample-laying part is disposed on the sample support; and the force-applying part is disposed on the sample-laying part. Resin concrete is poured onto the sample-laying part to form a test sample; the test sample is fixed on the sample support, and measured by pressing the force-applying part. Specifically, the resin concrete is laid on the sample-laying part, cured, fixed on the sample support, and loaded with a level of stress sustained by the force-applying part at a set frequency. The sample-laying part is disposed on the sample support, so that a gap is formed between the resin concrete and the ground or the sample support. The resin concrete, which comes in a variety of sizes and shapes, is free to deform in the space.

In a class of this embodiment, the sample-laying part comprises a substrate plate and at least two arms disposed on the substrate plate. The substrate plate is used to simulate a bridge deck and is sized according to the size of the resin concrete. The substrate plate comprises a first surface and a second surface opposite to the first surface; the at least two arms are disposed on both ends of the first surface, respectively. In certain examples, 3-5 arms are disposed on the substrate plate and a large format concrete slab is suspended above the sample support. The sample-laying part further comprises a detachable concrete mold for preparing the resin concrete in a variety of shapes and sizes. Before pouring the resin concrete, the detachable concrete mold is disposed on the second surface of the substrate plate.

In a class of this embodiment, the sample support comprises a bed plate and at least four roller assemblies disposed on the bed plate; each roller assembly comprises a roller, a roller support, and an adjusting bolt. The roller support is disposed on the bed plate; the roller is disposed on the roller support; the adjusting bolt is disposed between the roller and the roller support; and the sample support further comprises at least one barrier whose both ends are connected to two adjacent roller supports, respectively. The bed plate is used to support the weight of the entire device for fatigue test. The roller support is used to keep a distance between the bed plate and the sample-laying part. The height of the roller support increases with the increasing distance. The roller support is further used to position the roller and limit its rotary direction. In certain examples, four roller supports are disposed at four corners of the bed plate and rotates in the same direction. The roller rotates around its own axis without causing bending moments and is in surface contact with the at least one arm to support the sample-laying part. As the roller rotates, the at least one arms moves, causing the resin concrete to move synchronously. Thus, the device for fatigue test is used to measure the strength on each point above the surface of the resin concrete with different sizes, improving accuracy of the fatigue test. The adjusting bolt is used to prevent the rotation of the roller, thus preventing the resin concrete from sliding back and forth. The at least one barrier is used to prevent the resin concrete from sliding down the sample support. In certain examples, the sample support comprises four barriers disposed around the resin concrete to restrict the movement range, improving the fatigue test accuracy.

In a class of this embodiment, the force-applying part comprises a power part, a connecting shaft, and a press block. The force-applying part is used to apply stress of various levels, strengths, frequencies, and directions. One end of the connecting shaft is connected to the power part, and the other end of the connecting shaft is connected to the press block; the press block is used to transfer the stress of various levels, strengths, frequencies, and directions from the connecting shaft to the resin concrete. The resin concrete is in surface contact with the press block and withstands a stress level. The size and shape of the contact are determined for an accurate fatigue test according to the loading conditions and the specification of the press block.

The disclosure further provides a fatigue test method using the device for fatigue test, the method comprising:
  S10. removing rust from a steel plate by shot blasting;
  S20. applying a resin waterproof adhesive on the substrate plate;
  S30. pouring resin concrete on the substrate plate to form a test sample;
  S40. assembling the device for fatigue test around the resin concrete; and
  S50. loading the test sample at a temperature of 60° C. to 90° C. for fatigue test with the device.

The substrate plate is a steel plate or a substitute thereof. Specifically, the method involves removing rust from the steel plate, laying a layer of the resin waterproof adhesive onto the surface of the steel plate; and laying at least one layer of the resin concrete onto the layer of the resin waterproof adhesive to form a test sample. The steps S10-S30 simulate the process of laying the resin concrete to the bridge deck. Optically, the resin concrete is laid on the sample-laying part at high temperatures to increase the demand for a high temperature fatigue test. In S40, the force-applying part is disposed on the sample-laying part, and the sample-laying part is disposed on the sample support. In S50, the device for fatigue test uses the force-applying part to apply stress on the test sample at a controlled temperature.

Further, after rust removal, the steel plate has a surface roughness of 50-100 μm and meets a clearness standard Sa2.5. Otherwise, the resin concrete may fall or slip from the steel plate, resulting in a low fatigue test accuracy.

Further, the usage amount of the resin waterproof adhesive is 0.1-1.0 kg/m². The resin waterproof adhesive is used to prevent corrosion in the substrate plate and enhance the adhesion strength between the substrate plate and the resin concrete. Too much or too little adhesive between the bottom and the resin concrete can result in bond failure.

Further, pouring resin concrete on the substrate plate comprises stirring and laying at least one layer of the resin concrete on the substrate plate. Thereafter, the resin concrete is cured for fatigue test at a controlled temperature.

Further, pouring resin concrete on the substrate plate comprises:
S10. disposing a detachable concrete mold on the substrate plate whereby a space is formed therebetween;
S20. placing a reinforcing mesh in the space, and spraying the resin waterproof adhesive on the reinforcing mesh; and
S30. pouring the resin concrete into the space.

The reinforcing mesh comprises a steel reinforcing mesh.

A fluid resin concrete is poured into the detachable concrete mold and solidifies into the shape of the detachable concrete mold. The reinforcing mesh, such as a steel mesh or fiber glass cloth, is used for reinforcement of a resin concrete structure. The reinforcing mesh comprises a plurality of metals disposed between the top and bottom layers of the resin concrete. The resin waterproof adhesive is sprayed onto the surface of the reinforcing mesh to waterproof the plurality of metals and the substrate plate. The resin concrete is poured into the space once or multiple times, and the constituents of the resin concrete may vary each time.

Further, loading the test sample employs pneumatic loading, hydraulic loading, or a combination thereof; and the fatigue test is performed under a sinusoidal cyclic loading at a controlled temperature. The power part is compatible with other devices to power the test sample. The frequency and amplitude of the sinusoidal cyclic loading is adjustable according to the performance parameters of the test sample.

Figure 1:
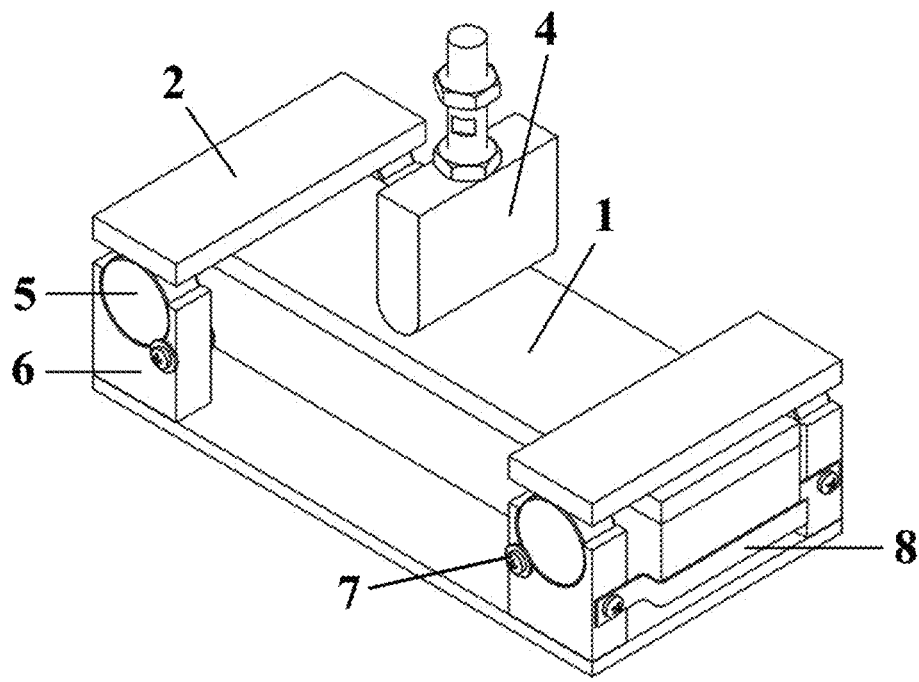
FIG. 1 is a perspective view of a device for fatigue test according to one example of the disclosure.

In the drawings, the following reference numbers are used: 1. Substrate plate; 2. Arm; 3. Resin concrete; 4. Press block; 5. Roller; 6. Roller support; 7. Adjusting bolt; 8. Barrier; and 9. Bed plate.

DETAILED DESCRIPTION OF THE EMBODIMENTS

To further illustrate the disclosure, embodiments detailing a device and method for high temperature fatigue test of resin concrete are described below. It should be noted that the following embodiments are intended to describe and not to limit the disclosure.

Example 1

Figure 2:
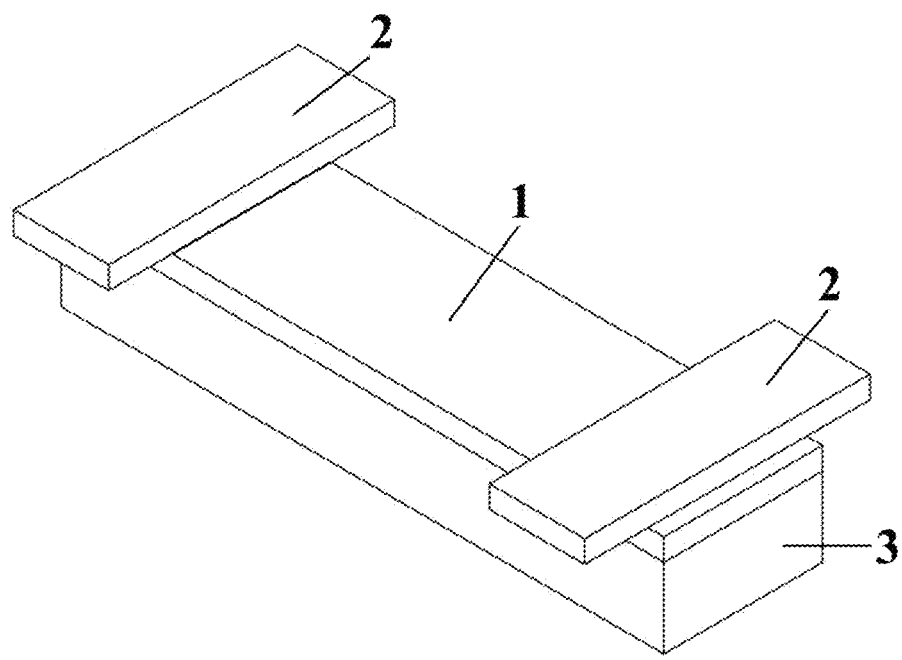
FIG. 2 is a perspective view of a sample-laying part according to one example of the disclosure.

As shown in FIGS. 1-2, a fatigue testing machine comprises a sample-laying part, a force-applying part, and a sample support. The sample-laying part comprises a substrate plate 1 and two arms 2. The substrate plate 1 comprises a first surface and a second surface opposite to the first surface. The two arms 2 are disposed on both ends of the first surface of the substrate plate 1, respectively. At least one layer of resin concrete is poured onto the second surface of the substrate plate 1, cured, and faced downward. The force-applying part applies a cyclic loading on the substrate plate 1 at a specific temperature.

Example 2

Figure 3:
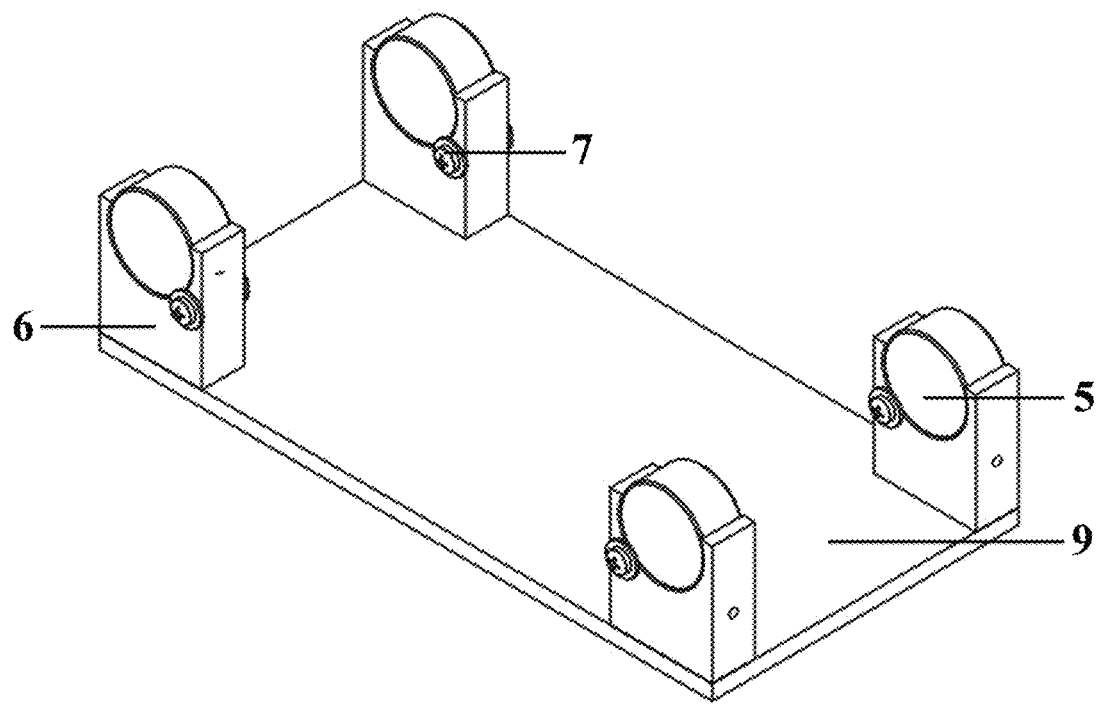
FIG. 3 is a perspective view of a sample support according to one example of the disclosure.

As shown in FIGS. 1 and 3, the fatigue testing machine comprises a sample-laying part, a force-applying part, four rollers 5, four roller supports 6, four adjusting bolts 7, and a bed plate 9. The four roller supports 6 are disposed at four corners of the bed plate 9, respectively, and always do face rolling upward in one direction. The four rollers 5 are disposed on the four roller supports 6, respectively. The sample support is disposed on the four rollers 5 and moves in the forward direction of the four rollers 5.

The four adjusting bolts 7 are used to prevent the rotation of the four rollers 5, respectively, so that the sample-laying part is at rest on the four rollers 5. The force-applying part applies a cyclic loading on the sample-laying part to perform the fatigue test.

Example 3

Figure 4:
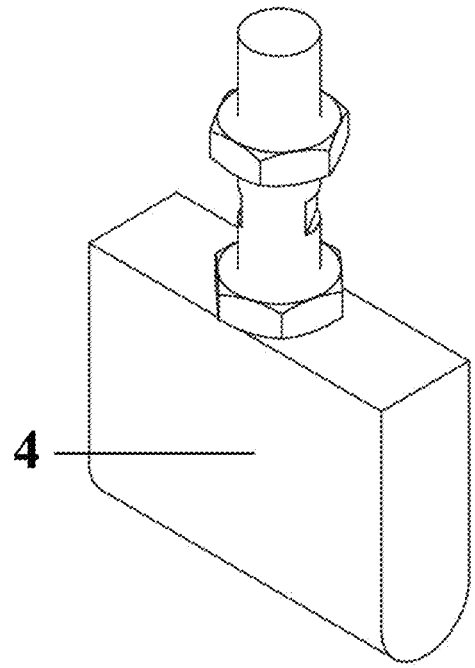
FIG. 4 is a perspective view of a force-applying part according to one example of the disclosure.

As shown in FIGS. 1 and 4, a fatigue testing machine comprises a sample-laying part, a sample support, a power part, a connecting shaft, and a press block 4. At least one layer of resin concrete is poured onto the sample-laying part and allowed to cure. The sample-laying part is then fixedly disposed on the sample support. The power part is used to set the frequency and amplitude for a load. The press block 4 and the power part are connected to both ends of the connecting shaft, respectively. The press block 4 sustains stress on the resin concrete to perform a fatigue test.

Example 4

As shown in FIGS. 1, 2, 3, and 4, a fatigue testing machine comprises a substrate plate 1, two arms 2, a concrete slab 3, a press block 4, four rollers 5, four roller supports 6, four adjusting bolts 7, two barriers 8, a bed plate 9, and a detachable concrete mold. The substrate plate 1, the two arms 2, and the detachable concrete mold constitute a sample-laying part. The concrete slab 3, the substrate plate 1, and the two arms 2 constitute a test sample. As shown in FIG. 2, the two arms 2 are welded to both ends of the first surface of the substrate plate 1, respectively; the detachable concrete mold is disposed on the second surface of the bottom surface 1 to form a space; at least one layer of resin concrete is poured into the space and allowed to cure; the detachable concrete mold is then removed, and the test sample is formed for fatigue test. The four rollers 5, the four roller supports 6, the four adjusting bolts 7, the two barriers 8, and the bed plate 9 constitute a sample support. As shown in FIG. 3, the four roller supports 6 are fixedly disposed at four corners of the bed plate 9, respectively; the four rollers 5 are disposed on the four roller supports 6, respectively; each of the four adjusting bolts 7 is disposed between each roller supports 6 and the corresponding roller 5. The sample-laying part is disposed on the sample support, and the four rollers 5 support the two arms 2. Two adjacent roller supports are connected via one of the two barriers 8 so as to prevent the movement of the support frame. The press block 4 sustains stress on the first surface of the substrate plate 1 to perform the fatigue test.

Example 5

A fatigue test method comprises:
S10. selecting a steel plate of a suitable size as a substrate plate 1; performing shot blasting to remove rust from the steel plate, thus making the steel plate achieve a surface roughness of 50-100 μm and comply with cleanliness standard Sa2.5;
S20. applying a layer of resin waterproof adhesive on the second surface of the substrate plate 1; the amount of the resin waterproof adhesive is 0.1-1.0 kg/m$^2$;
S30. pouring the resin concrete into the space surrounded by the substrate plate 1 and the concrete model; curing the resin concrete to form a concrete slab 3; removing the concrete model, thus forming a test sample comprising the substrate plate 1, the two arms 2, and the concrete slab 3;
S40. placing the test sample on the sample support; tightening the corresponding adjusting bolt 7 to lick the four rollers 5; and the two barriers 8 keep the test sample stationary;
S50. connecting the press block 4 to the fatigue testing machine comprising a temperature control system; placing the test sample into the fatigue testing machine; setting a loading temperature; pneumatically applying a sinusoidal cyclic load by the press block 4, thus applying a transverse linear stress on the center of the test sample; and the test sample is supported by the two arms 2;

Example 6

A fatigue test method comprises:
S10. selecting a steel plate of a suitable size as a substrate plate 1; performing shot blasting to remove rust from the steel plate, thus making the steel plate achieve a surface roughness of 50-100 μm and comply with cleanliness standard Sa2.5;
S20. applying a layer of resin waterproof adhesive on the second surface of the substrate plate 1; the amount of the resin waterproof adhesive is 0.1-1.0 kg/m$^2$;
S30. placing a spacer on the second surface of the substrate plate 1; placing a steel mesh in the concrete model; applying a layer of resin waterproof adhesive on the steel mesh; pouring the resin concrete into the space surrounded by the substrate plate 1 and the concrete model; curing the resin concrete to form a concrete slab 3; removing the concrete model, thus forming a test sample comprising the substrate plate 1, the two arms 2, and the concrete slab 3;
S40. placing the test sample on the sample support; tightening the corresponding adjusting bolt 7 to lick the four rollers 5; and the two barriers 8 keep the test sample stationary;
S50. connecting the press block 4 to the fatigue testing machine comprising a temperature control system; placing the test sample into the fatigue testing machine; setting a loading temperature; pneumatically applying sinusoidal cyclic load by the press block 4, thus applying a transverse linear stress to the center of the test sample; and the test sample is supported by the two arms 2.

Ten groups of high-temperature fatigue tests are respectively performed on resin concrete using the disclosed fatigue test method (Test method 2) and a conventional fatigue test method (Test method 1). The conventional fatigue test method comprises: arranging four loading devices spaced equally in a linear; the two loading devices on both sides are used to fix the test sample, and the other loading devices in the middle are used to apply the same repeated sinusoidal loading with a frequency of 5-25 Hz on the test sample; the conventional fatigue test is performed at 60-90° C.

Figure 5:
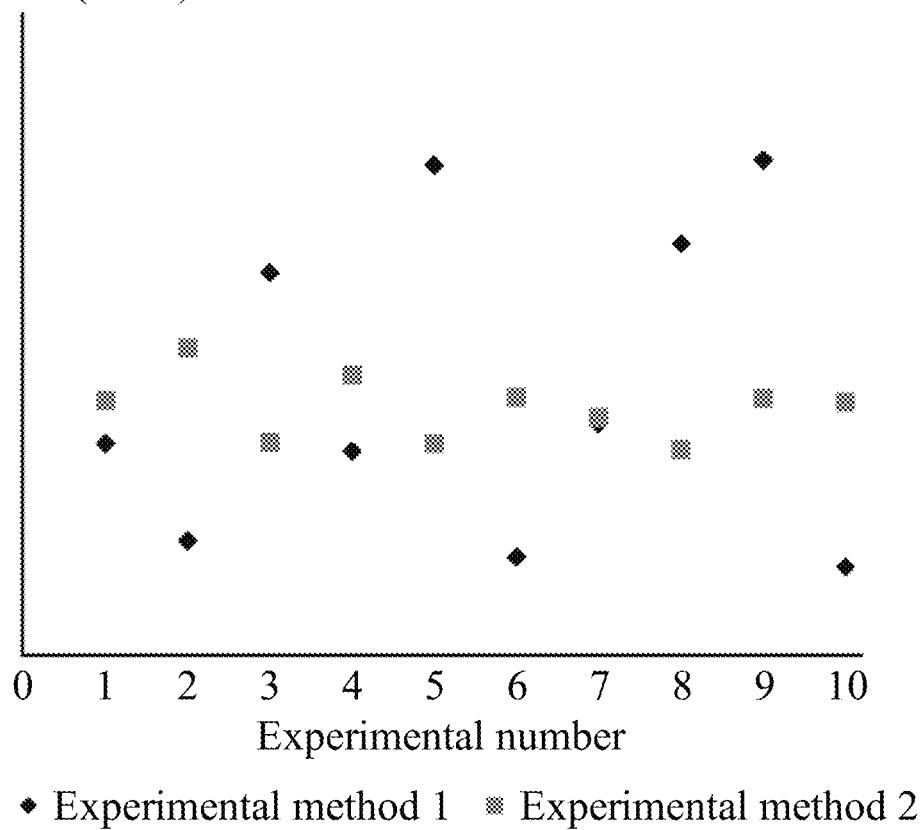
FIG. 5 is a comparison between experimental results according to one example of the disclosure.

Table 1 shows the fatigue test results for the test sample. Table 2 shows the analysis of the fatigue test results for the test sample. FIG. 5 depicts a comparison between fatigue test results.

TABLE 1

Fatigue test results for the test sample.

| No. | Results | |
| --- | --- | --- |
|  | Test method 1 | Test method 2 |
| 1 | 4823474 | 4992165 |
| 2 | 4443924 | 5194934 |
| 3 | 5489619 | 4826699 |
| 4 | 4793356 | 5090955 |
| 5 | 5908863 | 4823420 |
| 6 | 4380798 | 5003892 |
| 7 | 4900245 | 4924188 |
| 8 | 5602713 | 4800739 |
| 9 | 5928552 | 5000850 |
| 10 | 4341699 | 4984911 |

TABLE 2

Analysis of the fatigue test results for the test sample.

| Statistical indicator | Test method 1 | Test method 2 |
| --- | --- | --- |
| Average | 5061324 | 4964275 |
| Standard deviation | 588509 | 118525 |
| Range | 1586853 | 394195 |

As shown in Table 2 and FIG. 5, the standard deviation in the conventional fatigue test is five times that of the disclosed fatigue test, indicating that the disclosed fatigue test produces a more accurate result.

Example 7

A fatigue test method comprises:

S10. selecting a steel plate of a suitable size as a substrate plate 1; performing shot blasting to remove rust from the steel plate, thus making the steel plate achieve a surface roughness of 50-100 μm and comply a cleanliness standard Sa2.5;

S20. applying a layer of resin waterproof adhesive on the second surface of the substrate plate 1; the amount of the resin waterproof adhesive is 0.1-1.0 kg/m$^2$;

S30. pouring the resin concrete into the space surrounded by the substrate plate 1 and the concrete model, thus forming a first layer of the resin concrete; placing fiber glass cloth on the first layer of the resin concrete; pouring the resin concrete above the first layer of resin concrete; curing the resin concrete to form a concrete slab 3; removing the concrete model; the substrate plate 1, the two arms 2, and the concrete slab 3 constitute a test sample;

S40. placing the test sample on the sample support; tightening the corresponding adjusting bolt 7 to lick the four rollers 5; and the two barriers 8 keep the test sample stationary;

S50. connecting the press block 4 to the fatigue testing machine comprising a temperature control system; placing the test sample into the fatigue testing machine; setting temperature and load; pneumatically applying sinusoidal cyclic load by the press block 4, thus applying a transverse linear stress to the center of the test sample; and the test sample is supported by the two arms 2.

It will be obvious to those skilled in the art that changes and modifications may be made, and therefore, the aim in the appended claims is to cover all such changes and modifications.

What is claimed is:

1. A device for fatigue test, comprising:
a sample support;
a sample-laying part disposed on the sample support; and
a force-applying part disposed on the sample-laying part; wherein:
the sample-laying part comprises a substrate plate and at least two arms disposed on the substrate plate;
the sample support comprises a bed plate and at least four roller assemblies disposed on the bed plate; each roller assembly comprises a roller, a roller support, and an adjusting bolt; the roller support is disposed on the bed plate; the roller is disposed on the roller support; the adjusting bolt is disposed between the roller and the roller support; and
the sample support further comprises at least one barrier, and both ends of the barrier are connected to two adjacent roller supports, respectively.

2. The device of claim 1, wherein the force-applying part comprises a power part, a connecting shaft, and a press block; one end of the connecting shaft is connected to the power part, and the other end of the connecting shaft is connected to the press block.

3. A method for fatigue test of resin concrete using the device of claim 1, the method comprising:
S10. removing rust from a steel plate;
S20. applying a resin waterproof adhesive on the substrate plate;
S30. pouring resin concrete on the substrate plate to form a test sample;
S40. assembling the device around the resin concrete; and
S50. loading the test sample at a temperature of 60° C. to 90° C. for fatigue test with the device.

4. The method of claim 3, wherein after rust removal, the steel plate has a surface roughness of 50-100 μm and meets a clearness standard Sa2.5.

5. The method of claim 3, wherein a usage amount of the resin waterproof adhesive is 0.1-1.0 kg/m$^2$.

6. The method of claim 3, wherein pouring resin concrete on the substrate plate comprises stirring and laying at least one layer of the resin concrete on the substrate plate.

7. The method of claim 6, wherein pouring resin concrete on the substrate plate comprises:
disposing a detachable concrete mold on the substrate plate whereby a space is formed therebetween;
placing a reinforcing mesh in the space, and spraying the resin waterproof adhesive on the reinforcing mesh; and
pouring the resin concrete into the space.

8. The method of claim 3, wherein loading the test sample employs pneumatic loading, hydraulic loading, or a combination thereof; and the fatigue test is performed under a sinusoidal cyclic loading at a controlled temperature.

* * * * *